US011781141B2

(12) United States Patent
Bradburne et al.

(10) Patent No.: US 11,781,141 B2
(45) Date of Patent: Oct. 10, 2023

(54) INFLUENZA-ACTIVATED CONSTRUCTS AND METHODS OF USE THEREOF

(71) Applicant: The Johns Hopkins University, Baltimore, MD (US)

(72) Inventors: Christopher E. Bradburne, Ellicott City, MD (US); Lucy M. Carruth, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 483 days.

(21) Appl. No.: 16/908,346

(22) Filed: Jun. 22, 2020

(65) Prior Publication Data

US 2020/0318117 A1    Oct. 8, 2020

Related U.S. Application Data

(62) Division of application No. 14/768,465, filed as application No. PCT/US2014/023521 on Mar. 11, 2014, now Pat. No. 10,731,161.

(60) Provisional application No. 61/776,381, filed on Mar. 11, 2013.

(51) Int. Cl.
*C12N 15/113* (2010.01)
*C12Q 1/70* (2006.01)

(52) U.S. Cl.
CPC .......... *C12N 15/1131* (2013.01); *C12Q 1/701* (2013.01); *C12N 2310/14* (2013.01); *C12N 2310/317* (2013.01); *C12N 2310/336* (2013.01); *C12N 2310/531* (2013.01); *C12N 2320/30* (2013.01); *C12Q 2600/158* (2013.01); *C12Q 2600/178* (2013.01)

(58) Field of Classification Search
CPC .......... C12N 15/1131; C12N 2310/317; C12N 2310/336; C12N 2310/531; C12N 2320/30; C12N 2310/14; C12Q 1/701; C12Q 2600/158; C12Q 2600/178
See application file for complete search history.

(56) References Cited

U.S. PATENT DOCUMENTS

| | | | |
|---|---|---|---|
| 7,923,547 B2 | 4/2011 | McSwiggen et al. | |
| 7,956,178 B2 | 6/2011 | McSwiggen et al. | |
| 8,017,763 B2 | 9/2011 | Manoharan et al. | |
| 8,198,256 B2 | 6/2012 | Nakazawa et al. | |
| 8,227,188 B2 | 7/2012 | de Fougerolles et al. | |
| 8,377,901 B2 | 2/2013 | Coombs et al. | |
| 2003/0099670 A1 | 5/2003 | Hobom et al. | |
| 2007/0099858 A1 | 5/2007 | Jadhav et al. | |
| 2007/0197460 A1 | 8/2007 | Fougerolles et al. | |
| 2008/0076116 A1 | 3/2008 | Pekosz et al. | |
| 2008/0081791 A1 | 4/2008 | Huang et al. | |
| 2009/0062228 A1 | 3/2009 | Hannon et al. | |
| 2009/0313712 A1 | 12/2009 | Christmann et al. | |
| 2010/0204297 A1 | 8/2010 | Chen et al. | |
| 2011/0118334 A1 | 5/2011 | Iversen | |
| 2011/0281271 A1 | 11/2011 | Kohara et al. | |
| 2011/0288154 A1 | 11/2011 | Strapps et al. | |
| 2012/0009130 A1 | 1/2012 | Chakravarthy et al. | |
| 2012/0040459 A1 | 2/2012 | Khvorova et al. | |

FOREIGN PATENT DOCUMENTS

EP    2123758    11/2009

OTHER PUBLICATIONS

Boivin, S. et al., "Influenza A Virus Polymerase: Structural Insights into Replication and Host Adaptation Mechanisms," J Biol Chem., Jun. 10, 2010, vol. 285, No. 37, pp. 28411-28417.
Zhou, H. et al., "Effective small interfering RNAs targeting matrix and nucleocapsid protein gene inhibit influenza A virus replication in cells and mice," Antiviral Research 76 (2007) pp. 186-193.
Kumar, P. et al., "Potent inhibition of influenza virus replication with novel siRNA-chimeric-ribozyme constructs," Antiviral Research 87 (2010) pp. 204-212.
Ge, Q. et al., "Inhibition of influenza virus production in virus-infected mice by RNA interference," PNAS, vol. 101, No. 23, Jun. 8, 2004, pp. 8676-8681.
Tompkins, S.M. et al., "Protection against lethal influenza virus challenge by RNA interference in vivo," PNAS, vol. 101, No. 23, Jun. 8, 2004, pp. 8682-8686.
Ge, Q. et al., "RNA interference of influenza virus production by directly targeting mRNA for degradation and indirectly inhibiting all viral RNA transcription," PNAS, vol. 100, No. 5, Mar. 4, 2004, pp. 2718-2723.
Zhang, W. et al., "Inhibition of highly pathogenic avian influenza virus H5N1 replication by the small interfering RNA targeting polymerase A gene," Biochemical and Biophysical Research Communications 390 (2009) pp. 421-426.
Cheng, J.C. et al., "RNA interference and human disease," Molecular Genetics and Metabolism 80 (2003) pp. 121-128.
Ge, Q. et al., "Use of siRNAs to prevent and treat influenza virus infection," Virus Research 102 (2004) pp. 37-42.
Li, Y. et al., "Construction of Influenza Virus siRNA Expression Vectors and Their Inhibitory Effects on Multiplication of Influenza Virus," Avian Diseases 49 (2005) pp. 562-573.
Tado, M. et al., "Inhibitory effect of modified 5'-capped short RNA fragments on influenza virus RNA polymerase gene expression," Antiviral Chemistry & Chemotherapy 12 (2002) pp. 353-358 (1-6).
Zhou, K. et al., "RNA interference of avian influenza virus H5N1 by inhibiting viral mRNA with siRNA expression plasmids," Journal of Biotechnology 135 (2008) pp. 140-144.

*Primary Examiner* — J. E. Angell
(74) *Attorney, Agent, or Firm* — Sung T. Kim

(57) ABSTRACT

The presently disclosed subject matter provides a novel approach for the treatment, prevention, and diagnosis of Cap-Snatching virus infections, particularly all classes of human influenza, including pandemic influenza. The methods involve the use of constructs for RNA-interference (RNAi).

10 Claims, 3 Drawing Sheets

Specification includes a Sequence Listing.

INFLUENZA-ACTIVATED CONSTRUCTS AND METHODS OF USE THEREOF

CROSS-REFERENCE TO RELATED APPLICATIONS

This application is a divisional patent application of U.S. patent application Ser. No. 14/768,465, filed on Aug. 18, 2015, which claims priority to PCT Patent Application No. PCT/US14/23521, filed on Mar. 11, 2014, which claims priority to U.S. Provisional Patent Application No. 61/776,381, filed on Mar. 11, 2013, which are incorporated herein by reference in their entirety.

BACKGROUND OF THE INVENTION

1. Field of the Invention

This application is generally directed to the fields of molecular genetics and immunology. More particularly, this application is directed to RNAi precursor constructs that are activated in the presence of Cap-Snatching RNA viruses such as influenza.

2. Description of the Related Art

Influenza viruses have been a major cause of human mortality and morbidity throughout recorded history. Influenza A virus infection causes millions of cases of severe illness and as many as 500,000 deaths each year worldwide. The 1918 "Spanish" pandemic remains the worst example, causing upwards of 50 million deaths. Although vaccines against matched influenza strains can prevent illness in 60-80% of healthy adults, the rate of protection is much lower in high-risk groups. Furthermore, vaccination does not provide protection against unexpected strains, such as the H5 and H7 avian influenza outbreaks in Hong Kong in 1997 and Europe and Southeast Asia in 2003 and 2004. Current anti-influenza drugs are limited in their capacity to provide protection and therapeutic effect (Cox and Subbarao (1999) *Lancet* 354:1277-1282; Cox and Subbarao (2000) *Ann. Rev. Med.* 51:407-421).

Influenza A is a segmented RNA virus of negative-polarity. Genome segments are replicated by a complex of 4 proteins: the 3 polymerase polypeptides (PA, PB1 and PB2) and NP (Nucleoprotein). The 5' and 3' terminal sequence regions of all 8 genome segments are highly conserved within a genotype (Strauss and Strauss (2002) *Viruses and Human Disease*. San Diego, Academic Press). Influenza A viruses can be subtyped according to the antigenic and genetic nature of their surface glycoproteins; 15 hemagglutinin (HA) and 9 neuraminidase (NA) subtypes have been identified to date. Viruses bearing all known HA and NA subtypes have been isolated from avian hosts, but only viruses of the H1N1 (1918), H2N2 (1957/58), and H3N2 (1968) subtypes have been associated with widespread epidemics in humans (Strauss and Strauss (2002) *Viruses and Human Disease*. San Diego, Academic Press).

Influenza viruses infect humans and animals (e.g., pigs, birds, horses) and may cause acute respiratory disease. There have been numerous attempts to produce vaccines effective against influenza virus. None, however, have been completely successful, particularly on a long-term basis. This may be due, at least in part, to the segmented characteristic of the influenza virus genome, which makes it possible, through re-assortment of the segments, for numerous forms to exist. For example, it has been suggested that there could be an interchange of RNA segments between animal and human influenza viruses, which would result in the introduction of new antigenic subtypes into both populations. Thus, a long-term vaccination approach has failed, due to the emergence of new subtypes (antigenic "shift"). In addition, the surface proteins of the virus, hemagglutinin and neuraminidase, constantly undergo minor antigenic changes (antigenic "drift"). This high degree of variation explains why specific immunity developed against a particular influenza virus does not establish protection against new variants. Although influenza B and C viruses cause less clinical disease than the A types, new antiviral drugs could be helpful in curbing infections caused by these agents.

Only two classes of drugs are currently approved for the treatment of influenza: M2 ion channel blockers (adamantanes, in particular amantadine and rimantadine) and neuraminidase (NA) inhibitors (in particular oseltamivir and zanamivir) (De Clerq (2006) *Nat. Rev. Drug Discov.* 5:1015-1025). Adamantanes inhibit FluA replication by blocking virus entry, have no activity against FluB viruses, and are often associated with serious side effects and suffer from rapid emergence of drug-resistant viruses (Hayden & Hay (1992) *Curr. Top. Microbiol. Immunol.* 176:119-130). Neuraminidase inhibitors block the release of virions after budding from the host cell and exhibit activity against both FluA and FluB viruses, but have significant limitations such as causing side effects, susceptibility to resistance, inability to administer to children below 12 years old, and a required administration window within a few hours of infection (Colman et al. (1983) *Nature* 303:41-44; de Jong et al. (2005) *N. Engl. J. Med.* 353:2667-2672).

All influenzas, and many other (–) strand RNA viruses such as Hantaviruses, utilize a "Cap-Snatching" mechanism to prime the synthesis of their own RNA. Briefly, for influenza, this "Cap-Snatching" mechanism involves binding of host cellular mRNA to the inactive form of the influenza polymerase, which consists of 3 subunits: PB1, PB2, and PA. Binding of the PB1 subunit to viral, (–) strand RNA induced the PB2 subunit to bind a host cellular mRNA at the 5' end. The 3' end of the viral RNA then binds to a second site on the PB1 subunit, and the polymerase complex acquires the ability to cleave the 5' Cap, or "Cap-Snatch" the host cell mRNA cap. This cleavage results in a very specifically-lengthened fragment of 10-12 nucleotides. The Cap and 10-12 nucleotide sequence is then used to initiate, or "prime" synthesis of the virus' own RNA, resulting in a (+) strand which then serves as a template for further viral genomic (–) strand synthesis.

There is a need to develop new prophylactics, diagnostics, and treatments for influenza, particularly given the potential for pandemic influenza to emerge at any time. Of particular interest would be approaches that do not utilize the seasonally drifting and shifting viral coat proteins.

SUMMARY OF THE INVENTION

In some embodiments, the presently disclosed subject matter is directed to an expression vector comprising a polynucleotide coding sequence operably linked to a constitutive promoter, wherein the polynucleotide coding sequence encodes a precursor RNAi construct, wherein the precursor RNAi construct comprises an mRNA molecule comprising: (a) 5' methylguanosine cap leader; (b) an 8 to 12 nucleotide sequence immediately downstream from the methylguanosine cap leader; and (c) an RNAi sequence immediately downstream from the 8 to 12 nucleotide sequence; and wherein the mRNA molecule does not comprise a ribosomal binding site. In certain embodiments, the RNAi sequence is targeted to a transcript of the Cap-Snatching virus to inhibit replication of the Cap-Snatching virus. In other embodiments, the RNAi sequence is targeted to a sequence such that it activates one or more host cell response mechanisms against the Cap-Snatching virus. In other embodiments, the RNAi sequence targets host response transcripts to repress host responses during viral infection. In another embodiment, the RNAi sequence modulates a host immune response to prevent sepsis or cytokine storm. In other embodiments, the RNAi sequence is selected from the group consisting of an siRNA, an shRNA, a piRNA, an endo-siRNA, and an ra-siRNA. In further embodiments, the expression vector is a DNA vector or a lentiviral expression vector. In other embodiments, the Cap-Snatching virus is selected from the group consisting of an influenza virus, a hantavirus, a Rift Valley Fever virus, and a Cap-Snatching hemorrhagic virus. In further embodiments, the Cap-Snatching virus is an influenza virus, and the RNAi sequence is targeted to an influenza virus transcript, particularly wherein the RNAi sequence is an siRNA sequence selected from the group consisting of: SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. In other embodiments, the expression vector is a lentiviral expression vector that targets host epithelial airway cells but does not integrate into host epithelial airway cell DNA, particularly wherein the host epithelial airway cell is a human epithelial airway cell.

In some embodiments, the presently disclosed subject matter is directed to a method of treating or preventing an influenza infection in a subject in need thereof, the method comprising administering to the subject a prophylactically or therapeutically effective amount of a pharmaceutically acceptable composition comprising an expression vector comprising a polynucleotide coding sequence operably linked to a constitutive promoter, wherein the polynucleotide coding sequence encodes a precursor RNAi construct, wherein the precursor RNAi construct comprises an mRNA molecule comprising: (a) 5' methylguanosine cap leader; (b) an 8 to 12 nucleotide sequence immediately downstream from the methylguanosine cap leader; and (c) an RNAi sequence immediately downstream from the 8 to 12 nucleotide sequence; and wherein the mRNA molecule does not comprise a ribosomal binding site. In certain embodiments, the RNAi sequence is targeted to a transcript of the Cap-Snatching virus to inhibit replication of the Cap-Snatching virus. In other embodiments, the RNAi sequence is targeted to a sequence such that it activates one or more host cell response mechanisms against the Cap-Snatching virus. In other embodiments, the RNAi sequence targets host response transcripts to repress host responses during viral infection. In another embodiment, the RNAi sequence modulates a host immune response to prevent sepsis or cytokine storm. In other embodiments, the RNAi sequence is selected from the group consisting of an siRNA, an shRNA, a piRNA, an endo-siRNA, and an ra-siRNA. In further embodiments, the expression vector is a DNA vector or a lentiviral expression vector. In other embodiments, the Cap-Snatching virus is selected from the group consisting of an influenza virus, a hantavirus, a Rift Valley Fever virus, and a Cap-Snatching hemorrhagic virus. In further embodiments, the Cap-Snatching virus is an influenza virus, and the RNAi sequence is targeted to an influenza virus transcript, particularly wherein the RNAi sequence is an siRNA sequence selected from the group consisting of: SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. In other embodiments, the expression vector is a lentiviral expression vector that targets host epithelial airway cells but does not integrate into host epithelial airway cell DNA, particularly wherein the host epithelial airway cell is a human epithelial airway cell. In other embodiments, the pharmaceutically acceptable composition is administered to airway epithelial cells of a subject to treat or prevent an influenza infection, particularly to nasal or intrapulmonary airway epithelial cells of the subject by direct topical application or by inhalation.

In some embodiments, the presently disclosed subject matter is directed to a method of diagnosing a Cap-Snatching virus infection in a subject, the method comprising: (a) obtaining a biological sample from the subject, wherein the biological sample comprises cells suspected of being infected with a Cap-Snatching virus; (b) introducing a first expression vector into the cells, wherein the first expression vector comprises a first polynucleotide coding sequence operably linked to a constitutive promoter, wherein the first polynucleotide coding sequence encodes an expression product capable of producing a detectable signal, and further wherein the detectable signal is produced from the expression product in the cells; (c) obtaining a first measurement of the detectable signal produced from the expression product in the cells; (d) introducing a second expression vector into the cells, wherein the second expression vector comprises a polynucleotide coding sequence encoding a precursor RNAi construct, wherein the precursor RNAi construct comprises an mRNA molecule comprising: (i) a 5' methylguanosine cap leader; (ii) an 8 to 12 nucleotide sequence immediately downstream from the methylguanosine cap leader; and (iii) an RNAi sequence immediately downstream from the 8 to 12 nucleotide sequence, wherein the RNAi sequence is targeted to the expression product that produces a detectable label; and (e) obtaining a second measurement the detectable signal produced from the expression product in the cells; wherein a decrease in the detectable signal from the first measurement to the second measurement is indicative of a Cap-Snatching virus infection in the subject. In one embodiment, the expression product that produces a detectable label is Green Fluorescent Protein (GFP). In other embodiments, the RNAi sequence is selected from the group consisting of an siRNA, an shRNA, a piRNA, an endo-siRNA, and an ra-siRNA. In further embodiments, the expression vector is a DNA vector or a lentiviral expression vector. In other embodiments, the Cap-Snatching virus is selected from the group consisting of an influenza virus, a hantavirus, a Rift Valley Fever virus, and a Cap-Snatching hemorrhagic virus, particularly wherein the Cap-Snatching virus is an influenza virus, and more particularly wherein the cells comprise airway epithelial cells suspected of being infected with an influenza virus.

DETAILED DESCRIPTION OF THE INVENTION

Figures 1A, 1B:
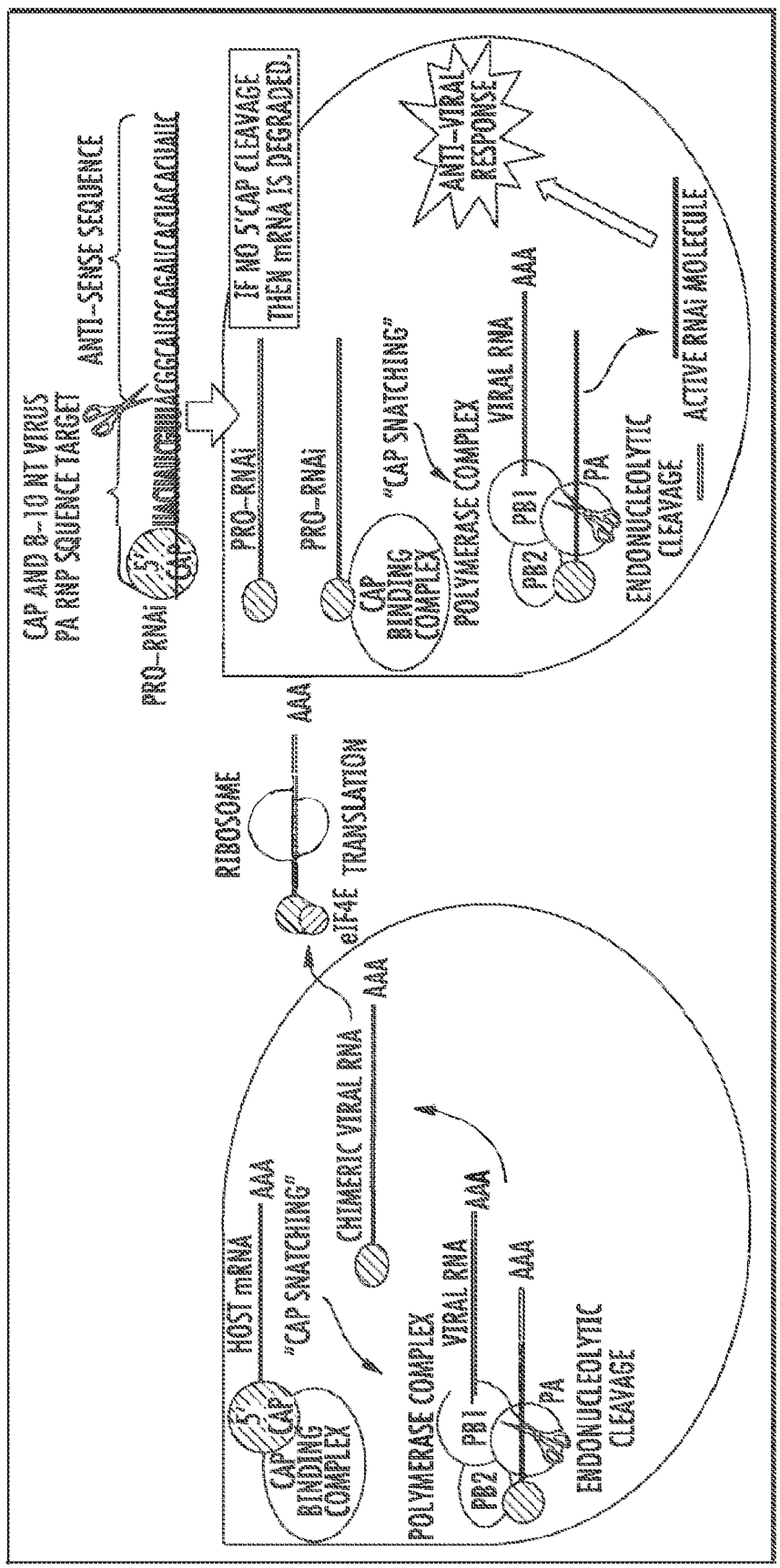
FIGS. 1A-1C show: A) normal virus Cap-Snatching to replicate its genome in a host epithelial cell; B) viral Cap-Snatching activates the pro-form anti-viral RNAi in a size-specific way; and C) the anti-viral response is cell specific, and proportional to the level of viral activity.
Figure 1C:
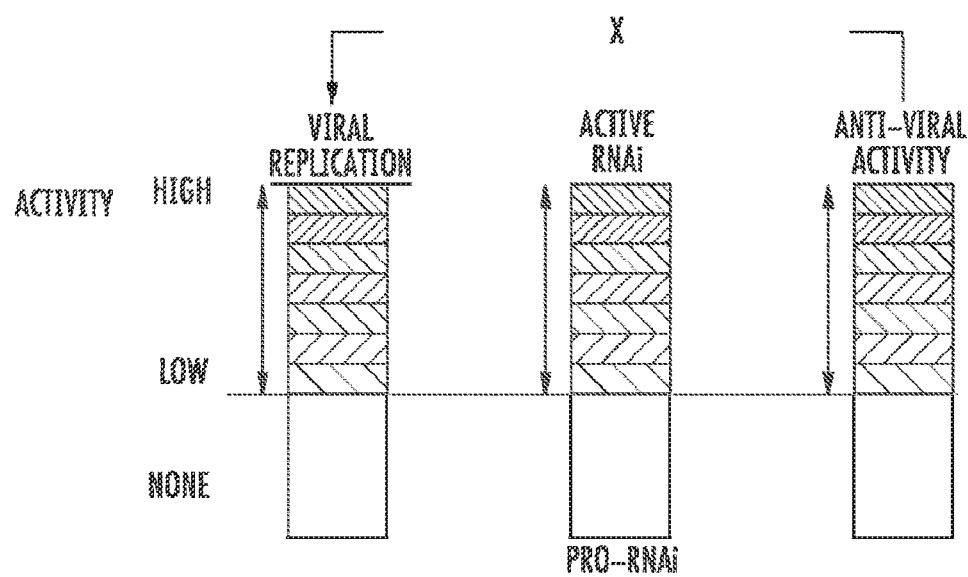
Figure 2:
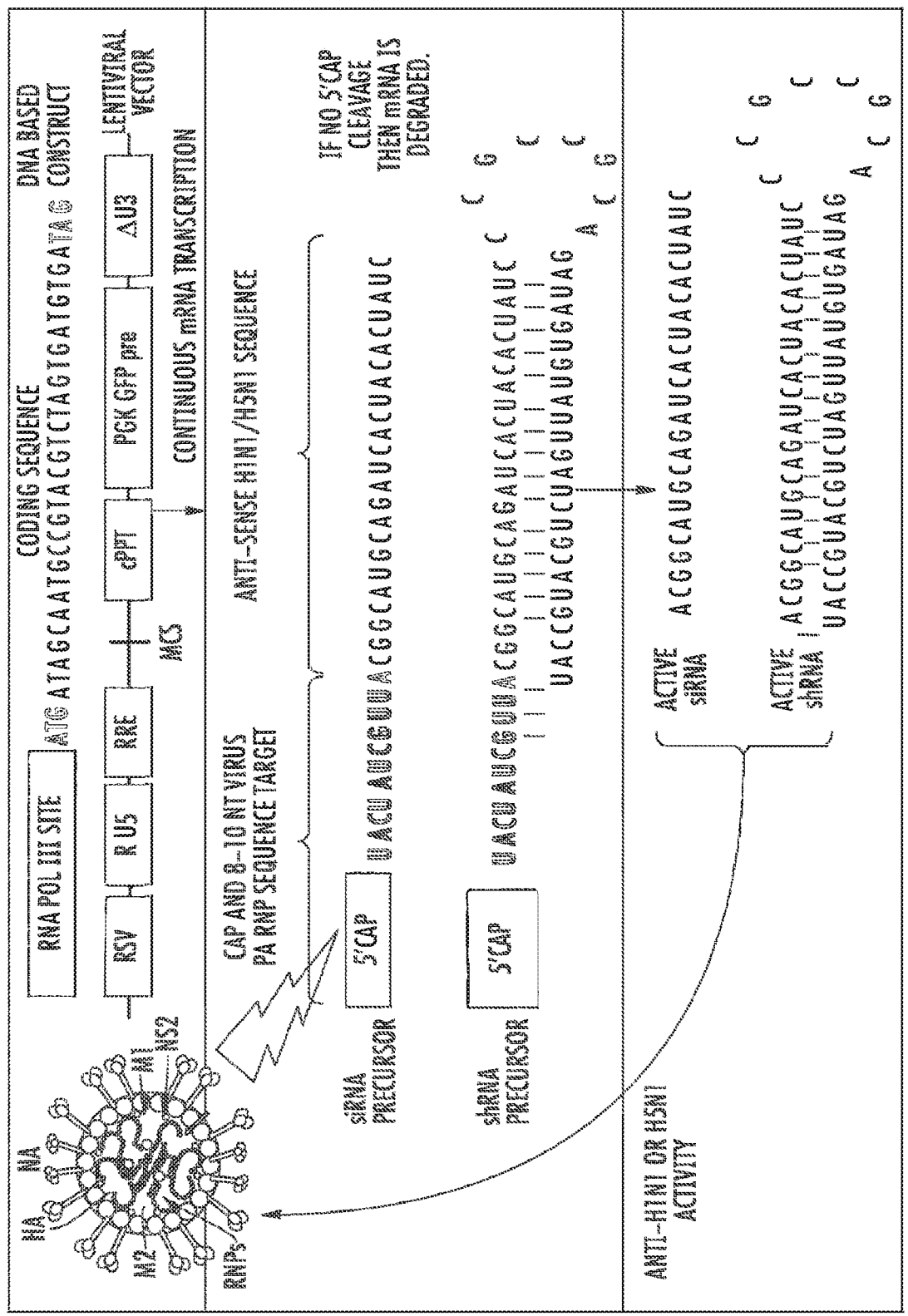
FIG. 2 shows a schematic of an exemplary DNA vector or lentiviral expression vector for use within the presently disclosed subject matter and the Cap-Snatching mechanism by which pro-form RNAi are activated in the presence of Cap-Snatching viral machinery.

The presently disclosed subject matter provides a novel approach for the treatment, prevention, and diagnosis of Cap-Snatching virus infections, such as hantaviruses, Rift Valley Fever and some hemorrhagic fevers, and particularly all classes of human influenza, including pandemic influenza. The methods involve the use of constructs for virally-activated RNA-interference (RNAi).

"Cap-snatching" is a special mechanism of viral transcription initiation found among the segmented (−)ssRNA viruses and first discovered for Influenza A (Bouloy et al. (1978) *Proc. Natl. Acad. Sci. USA* 75:4886-4890; Plotch et al. (1979) *Proc. Natl. Acad. Sci. USA* 76:1618-1622; Krug et al. (1979) *Cell* 18:329-334; Caton and Robertson (1980) *Nucl. Acids Res.* 8:2591-2603; Dhar et al. (1980) *Cell* 21:495-500; Beaton and Krug (1981) *Nucl. Acids Res.* 9:4423-4436; Plotch et al. (1981) *Cell* 23:847-858). During this mechanism, the viral transcriptase cleaves $m^7$G-capped RNA leader sequences from host mRNAs to prime transcription of the viral genome. Nascent viral transcripts thereby are provided a 5' cap structure and a non-viral leader sequence, which allows them to be distinguished from (anti)genomic viral RNA molecules. Cap-snatching has later been reported for all segmented (−)ssRNA viruses irrespective of their host (animal, human or plants) (Kormelink et al. (1992) *J. Gen. Virol.* 73:2125-2128; Huiet et al. (1993) *Virology* 197:808-812; Jin and Elliott (1993) *J. Virol.* 67:1396-1404; Jin and Elliott (1993) *J. Gen. Virol.* 74:2293-2297; Garcin et al. (1995) *J. Virol.* 69:5754-5762; Duijsings et al. (1999) *J. Virol.* 73:5172-5175), with the exception of Ophioviruses.

Whereas most of these viruses replicate in the cytoplasm and use the existing pool of host mRNAs as substrate, Influenza A virus replicates in the nucleus of the infected cell where it uses nascently synthesized transcripts from the RNA polymerase II complex (Fodor et al. (2000) *EMBO Rep.* 1:513-518; Engelhardt et al. (2005) *J. Virol.* 79:5812-5818; Chan et al. (2006) *Virology* 351:210-217). During the last two decades, the use of various in vitro systems (Bouloy et al. (1978) *Proc. Natl. Acad. Sci. USA* 75:4886-4890; Plotch et al. (1979) *Proc. Natl. Acad. Sci. USA* 76:1618-1622; Hagen et al. (1994) *J. Virol.* 68:1509-1515) and the establishment of reverse genetics systems (Pleschka et al. (1996) *J. Virol.* 70:4188-4192; Fodor et al. (1999) *J. Virol.* 73:9679-9682; Neumann et al. (1999) *Proc. Natl. Acad. Sci. USA* 96:9345-9350) have advanced the insight into cis- and trans-acting factors involved in cap-snatching.

The Influenza A polymerase complex consists of three viral proteins, PB1, PB2 and PA, which are all required for viral mRNA synthesis. Whilst the role of PA is still unknown, PB2 binds to the 5' cap structure of cellular mRNAs (Licheng et al. (1995) *Virology* 208:38-47), which activates its endonuclease domain to cleave at a site 10-14 nucleotides downstream the 5' cap structure. During mRNA chain elongation, PB1 catalyses nucleotide addition (Braam et al. (1983) *Cell* 34:609-618). Whereas several reports suggested that the presence of the 5'terminal end of the viral RNA template (vRNA) is required and sufficient for activation of cap-dependent endonuclease activity (Hagen et al. (1994) *J. Virol.* 68:1509-1515; Cianci et al. (1995) *J. Virol.* 69:3995-3999), others have suggested that endonuclease activation requires a specific base pairing between several residues of the 5'- and 3'-terminal end of the vRNA template (Li et al. (2001) *EMBO J.* 20:2078-2086). Endonuclease cleavage generally takes place around 8-12 nucleotides from the 5' cap structure, particularly 10-12 nucleotides from the 5' cap structure.

Current RNAi technology involves activating the host RNAi machinery in both infected and non-infected host cells, exposing both types to potential toxicity and off-target effects that are common with RNAi-based therapies. The presently disclosed methods only allow for activation of RNAi machinery in infected cells and therefore allow for the treatment, prevention and/or diagnosis of virally-infected subjects and/or cells and tissues with minimal effects to the host since constructs are inactive unless in the presence of Cap-Snatching virus.

The presently disclosed methods utilize the very specific size of the viral Cap-Snatched sequence to activate a short RNAi. RNAi depends on short, double-stranded and sometimes single-stranded RNAs. All depend on a very specific sequence length to be active, a length that typically only varies by 4-5 nucleotides. In the presently disclosed methods, a DNA construct or viral construct is introduced to a subject and or/cell which constitutively expresses mRNA with the typical 5' Cap. This mRNA has an internal RNAi sequence which has been validated against a Cap-Snatching virus such as influenza, but that is too long to engage the RNAi machinery in the cell and is thus normally degraded by cellular machinery. This sequence does not contain a ribosomal binding site, and the start of the internal RNAi sequence is located 8-12 nucleotides from the 5' Cap.

In the presence of viral machinery (PB1/2), which binds the synthetic construct and cleaves the 5' Cap, the 10-12 nucleotides upstream of the RNAi sequence are removed, and the RNAi sequence achieves the correct length to become activated and engage the RNAi machinery in the cell. This results in a specific anti-Cap-Snatching response, which can serve as a therapeutic and is only activated in the presence of a Cap-Snatching virus. The presently disclosed method is self- and time-limited due to host cell turnover, such as intranasal or topical, with clearance in about 1 to 2 weeks. Further, the induction of activated, short RNAs can be tailored to reduce virus replication, as well as modulate host responses in general, including innate immunity, programmed-cell death (apoptosis), or any other regulatory host genetic elements applicable to fighting local or systemic disease via RNAi.

I. Compositions

In some embodiments, the presently disclosed subject matter is directed to an expression vector comprising a polynucleotide coding sequence operably linked to a constitutive promoter, wherein the polynucleotide coding sequence encodes a precursor RNAi construct, wherein the precursor RNAi construct comprises an mRNA molecule comprising: (a) 5' methylguanosine cap leader; (b) an 8 to 12 nucleotide sequence immediately downstream from the methylguanosine cap leader; and (c) an RNAi sequence immediately downstream from the 8 to 12 nucleotide sequence; and wherein the mRNA molecule does not comprise a ribosomal binding site. In some embodiments, the 8 to 12 nucleotide sequence immediately downstream from the methylguanosine cap leader may constitute 8, 9, 10, 11, or 12 nucleotides immediately downstream from the methylguanosine cap leader.

"Cap(ped)-leader sequence(s)" or "cap(ped)-leader(s)" or "leader sequence(s)" or cap(ped) RNA primers are herein defined as $m^7$ G-capped RNA sequences that can be used to prime transcription of the viral genome. The 5' cap is found on the 5' end of an mRNA molecule and consists of a 7-methylguanosine residue connected to the RNA via an unusual 5' to 5' triphosphate linkage (7MeGpppN). It is referred to as a 7-methylguanosine cap, abbreviated $m^7$ G-cap. After completion of transcription the viral RNA is provided with a non-viral (not originating from the virus itself) 5' cap structure and non-viral leader sequences. Cap-leaders are typically of host origin, and the process of initiation of viral transcription with a cap-leader sequence is also referred to as "Cap-Snatching".

The terms "RNA interference" and RNAi as used herein is a biological process by which RNA molecules inhibit gene expression, typically by causing the destruction of specific mRNA molecules, or by binding complementary nucleotide sequences and inhibiting their transcription or translation by polymerases or ribosomes, respectively. Some small RNA molecules, such as microRNA (miRNA) and small interfering RNA (siRNA), are central to RNA interference. These small RNAs can bind to other specific messenger RNA (mRNA) molecules and either increase or decrease their activity, for example by preventing an mRNA from producing a protein. RNA interference has an important role in defending cells against parasitic nucleotide sequences, such as viruses and transposons.

As described above, the presently disclosed constructs enable methods that utilize the intrinsic viral replication machinery required for viral replication and comprise a novel use of an evolutionarily conserved Cap-Snatching replication mechanism for RNAi activation in mammalian cells. In certain embodiments, the RNAi sequence is targeted to a transcript of the Cap-Snatching virus to inhibit replication of the Cap-Snatching virus. In other embodiments, the RNAi sequence is targeted to a sequence such that it activates one or more host cell response mechanisms against the Cap-Snatching virus. In other embodiments, the RNAi sequence targets host response transcripts to repress host responses during viral infection. In another embodiment, the RNAi sequence modulates a host immune response to prevent sepsis or cytokine storm.

Sepsis is clinically characterized as a systemic inflammatory response to infection, but it can also arise from trauma or injury (Tracey (2002) *Nature* 420:853-859; Ulloa and Tracey (2005) *Trends Mol. Med.* 1:56-63; Martin et al. (2003) *New England J. Med.* 348:1546-1554). Sepsis is clinically characterized as a systemic inflammatory response to infection, but it can also arise from trauma or injury (Tracey (2002) *Nature* 420:853-859; Ulloa and Tracey (2005) *Trends Mol. Med.* 1:56-63; Martin et al. (2003) *New England J. Med.* 348:1546-1554). Sepsis is a serious medical problem and scientific challenge with a significant unmet need, as it is the leading cause of death among patients in Intensive Care Units (ICU) worldwide. Mortality rates range from 20% for sepsis, to 40% for severe sepsis, and >60% for septic shock (Tracey (2002) *Nature* 420:853-859; Ulloa and Tracey (2005) *Trends Mol. Med.* 1:56-63; Martin et al. (2003) *New England J. Med.* 348:1546-1554). Current therapies target the symptoms of sepsis and are geared to support cardiovascular and respiratory function, but they do not specifically address the underlying causes of the inflammatory disease, which involves a dysregulated or poorly balanced innate inflammatory response (Tracey (2002) *Nature* 420:853-859; Ulloa and Tracey (2005) *Trends Mol. Med.* 1:56-63; Martin et al. (2003) *New England J. Med.* 348:1546-1554; Wang et al. (1999) *Science* 285:248-251; Tracey and Abraham (1999) *Shock,* 1:224-225; Andersson et al. (2000) *J. Exp. Med.* 192:565-570). The overall lack of improvement in sepsis survival rates, despite significant advances in supportive intensive care, indicates an unmet need in effective target-directed anti-sepsis therapies.

Sepsis is caused by the loss of homeostatic balance during the innate immune response to infection or injury (Tracey (2002) *Nature* 420:853-859; Ulloa and Tracey (2005) *Trends Mol. Med.* 1:56-63). The innate immune response is driven primarily by signaling molecules collectively referred to as cytokines, which are used by cells of the immune system to communicate the integrity of the body's barriers to the environment. Cytokines are normally produced by immune cells in response to pathogen-associated molecules (PAMPs) or damage-associated molecules (DAMPs), and activate other immune cells to increase the body's immune response. There are two main classes of clinically relevant cytokines: pro-inflammatory mediators that activate and amplify inflammation and anti-inflammatory mediators that impede and balance the inflammatory response. A predominant belief amongst immunologists is that an unrestrained pro-inflammatory mediator cascade causes disease (Tracey (2002) *Nature* 420:853-859; Ulloa and Tracey (2005) *Trends Mol. Med.* 1:56-63; Marshall et al. (1995) *Critical Care Medicine* 23:1638-1652; Riedemann et al. (2003) *Nature Medicine* 9:517-524; Tracey et al. (1987) *Nature* 330:662-664; Tracey et al. (1986) *Science* 234:470-474; Wang et al. (1999) *Science* 285:248-251; Tracey and Abraham (1999) *Shock,* 1:224-225; Andersson et al. (2000) *J. Exp. Med.* 192:565-570). The dysregulated sequence of proinflammatory cytokines leading to disease has been referred to as a "cytokine storm" or "inflammatory cascade," as one cytokine typically leads to the production of multiple other cytokines to reinforce and amplify the immune response (Ferrara et al. (1993) *Transplantation Proceedings* 25:1216-1217; Giroir (1993) *Critical Care Medicine* 21:780-789).

The RNAi sequence within the methods and compositions of the presently disclosed subject matter may be an siRNA, an shRNA, a piRNA, an endo-siRNA, and an ra-siRNA. The term "siRNA", "small interfering RNA", "short interfering RNA" or "silencing RNA" is intended to mean a class of double-stranded RNA molecules that are short in length, such as in some embodiments around 20 to 25 nucleotides in length. siRNA interferes with the expression of specific genes with a complementary nucleotide sequence.

The terms "small hairpin RNA", "short hairpin RNA", and shRNA as used herein refer to a sequence of RNA that makes a tight hairpin turn that can be used to silence target gene expression via RNA interference (RNAi).

Piwi-interacting RNA (piRNA) form RNA-protein complexes through interactions with piwi proteins. These piRNA complexes have been linked to both epigenetic and post-transcriptional gene silencing of retrotransposons and other genetic elements in germ line cells. piRNAs are slightly longer (about 24 to 32 nucleotides) than siRNAs (about 21 to 24 nucleotides).

Endo-siRNA are endogenous (originating in the host cell), such as pre-microRNAs expressed from RNA-coding genes in the host cell genome. The primary transcripts from such genes are first processed to form the characteristic stem-loop structure of pre-miRNA in the nucleus, then exported to the cytoplasm.

Repeat associated small interfering RNA (ra-siRNA) is a class of small RNA that is involved in the RNA interference (RNAi) pathway. Ra-siRNA are in fact Piwi-interacting RNAs. In the germline, RasiRNA is involved in establishing and maintaining heterochromatin structure, controlling transcripts that emerge from repeat sequences, and silencing transposons and retrotransposons.

A "host cell" as used herein refers to a cell that comprises a recombinant polynucleotide molecule, typically a recombinant plasmid or other expression vector. Thus, for example, host cells can express genes that are not found within the native (non-recombinant) form of the cell. According to the presently disclosed methods, the host cell is any cell that can host a virus in which its replicating genome reproduces by cap-snatching, such as a Type 1 or 2 epithelial airway cell for influenza infections.

The presently disclosed subject matter is applicable to any infectious viruses which exhibit Cap-Snatching activity, including, but not limited to, influenza, hantaviruses, Rift Valley Fever virus, and certain hemorrhagic viruses.

Influenza, commonly known as "the flu", is an infectious disease of birds and mammals caused by RNA viruses of the family Orthomyxoviridae, the influenza viruses. The most common symptoms are chills, fever, runny nose, sore throat, muscle pains, headache (often severe), coughing, weakness/fatigue and general discomfort.

Hantaviruses are single-stranded, enveloped, negative sense RNA viruses in the Bunyaviridae family. Humans may become infected with hantaviruses through contact with rodent urine, saliva, or feces. Some strains of hantaviruses cause potentially fatal diseases in humans, such as Hantavirus hemorrhagic fever with renal syndrome (HFRS) and hantavirus pulmonary syndrome (HPS), while others have not been associated with known human disease.

Rift Valley Fever virus belongs to the Phlebovirus genus of the Bunyaviridae family. It is transmitted by many species of mosquitoes, and periodically causes epidemics and epizootics in North Africa and the Arabian peninsula within periods of mosquito activities (Gad et al. (1987) *Trans. R. Soc. Trop. Med. Hyg.* 81:694-8; Meadors et al. (1986) *Vaccine* 4:179-84). Infection in humans provokes a wide range of symptoms, from benign febrile to fatal encephalitis, retinitis, and hepatitis associated with hemorrhages. In livestock and wild ruminants it causes teratogeny and abortion in pregnant animals and produces a high rate of mortality in young animals. The Rift Valley Fever virus is an enveloped virus of 90 to 110 nm in size, with a core element of 80 to 85 nm (Ellis et al. (1988) *J. Med. Virol.* 24:161-74; Ellis et al. (1979) *J. Gen. Virol.* 42:329-37). Its genome consists of single-stranded, tripartite RNA, among which the large (L) and the medium (M) segments are negative polarity, and the small (S) fragment is ambisense polarity. The L segment codes for the RNA-dependent RNA polymerase, which is packed together with the RNA fragments inside virus particles (Muller et al. (1994) *J. Gen. Virol.* 75:1345-52). The S segment encodes two proteins: the structural nucleoprotein (N) in the anti-genomic sense; and the non-structural (NS) protein in the genomic sense (Giorgi et al. (1991) *Virology* 180:738-53). The N protein is associated with genome RNA and packed inside of the virus particle, and the NS protein plays a role to block interferon production by inhibiting host gene transcription (Billecocq et al. (2004) *J. Virol.* 78:9798-806). The M segment codes for a polypeptide precursor, from which the structural glycoproteins (Gn and Gc) and two non-structural proteins (78 kDa and 14 kDa) are produced by cleavage (Collett (1986) *Virology* 151.151-6; Kakach et al. (1989) *Virology* 170:505-10; Suzich et al. (1988) *Virology* 164:478-86).

A cap-snatching mechanism similar to that in influenza virus has been proposed for all minus-strand segmented RNA viruses, including bunyaviruses and arenaviruses, in spite of the fact that their RNA-dependent RNA polymerases (RdRps) are structurally different and they replicate at different locations inside the host cell. In contrast to influenza virus, the RdRp of bunyaviruses and arenaviruses is encoded by one rather than three genes. Recent studies have also suggested that RdRp from bunyaviruses and arenaviruses harbors the endonuclease domain at the N terminus, and its endonuclease activity has been demonstrated. Moreover, influenza viruses carry out Cap-Snatching and transcription in the nucleus of infected cells while bunyavirus and arenavirus transcription and genome replication are cytoplasmic. Also, in contrast to influenza virus, the viruses carrying out Cap-Snatching in the cytoplasm have to compete with cellular RNA degradation machinery, which actively removes caps and degrades cellular transcripts after the completion of translation.

In particular embodiments of the presently disclosed subject matter, the Cap-Snatching virus is an influenza virus, and the RNAi sequence is targeted to an influenza virus transcript, particularly wherein the RNAi sequence is an siRNA sequence selected from the group consisting of: SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

In other embodiments, the expression vector is a lentiviral expression vector that targets host epithelial airway cells but does not integrate into host epithelial airway cell DNA, particularly wherein the host epithelial airway cell is a human epithelial airway cell. The adult human bronchial tree is covered with a continuous layer of epithelial cells that play a critical role in maintaining the conduit for air, and which are central to the defenses of the lung against inhaled environmental concomitants. The epithelial sheet functions as an interdependent unit with the other lung components. Importantly, the structure and/or function of airway epithelium is deranged in major lung disorders, including chronic obstructive pulmonary disease, asthma, and bronchogenic carcinoma.

As used interchangeably herein, the terms "nucleic acids," "oligonucleotides," and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT Patent App. Pub. No. WO 95/04064. The polynucleotide sequences of the presently disclosed subject matter may be prepared by any known method, including synthetic, recombinant, ex vivo generation, or a combination thereof, as well as utilizing any purification methods known in the art. A polynucleotide may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

The terms "complementary" or "complement thereof" are used herein to refer to the sequences of polynucleotides that are capable of forming Watson & Crick base pairing with another specified polynucleotide throughout the entirety of the complementary region. For the purpose of the presently disclosed subject matter, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide," "complementary nucleic acid" and "complementary nucleotide sequence". These terms are applied to pairs of polynucleotides based solely upon their sequences and not any particular set of conditions under which the two polynucleotides would actually bind.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo.

Accordingly, the terms "expression vector" and "expression construct" as used herein refer to a DNA construct for expression of an mRNA construct in cells. A number of suitable vectors are well-known and conventional in the art. Suitable vectors can contain a number of components, including, but not limited to one or more of the following: an origin of replication; one or more expression control elements, such as a transcriptional control element (e.g., a promoter, an enhancer, a terminator), and/or one or more translation signals; and a signal sequence or leader sequence for targeting to the secretory pathway in a selected host cell. If desired, the vector can include a detectable marker.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

In particular embodiments, the expression vector is a DNA vector or a lentiviral expression vector. Lentiviruses are a subclass of retroviruses that have the ability to integrate into the genome of non-dividing cells. They can be adapted as gene delivery vehicles or vectors. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides.

Viral vectors, and particularly retroviral vectors, have been used in a wide variety of gene delivery applications in cells, as well as living animal subjects. Viral vectors are well known in the art and include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), palmylated peptides, DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al. (1992) *J. Biol. Chem.* 267:963; Wu et al. (1988) *J. Biol. Chem.* 263:14621).

A precursor RNAi construct according to the presently disclosed subject matter can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Feigner et al. (1988) *Proc. Natl. Acad. Sci. USA* 84:7413; Mackey et al.

(1988) *Proc. Natl. Acad. Sci. U.S.A.* 85:8027; and Ulmer et al. (1993) *Science* 259:1745). The use of cationic lipids may promote encapsulation of negatively charged nucleic acids, and also promote fusion with negatively charged cell membranes (Feigner et al. (1989) *Science* 337:387). Particularly useful lipid compounds and compositions for transfer of nucleic acids are described in PCT Patent Pubs. WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. (1988) *Proc. Natl. Acad. Sci. U.S.A.* 85:8027). Targeted peptides, e.g., hormones or neurotransmitters, and proteins such as antibodies, or non-peptide molecules could be coupled to liposomes chemically.

Isolated and/or recombinant (including, e.g., essentially pure) nucleic acid molecules can be administered in situ or in vivo. Nucleic acid molecules referred to herein as "isolated" are nucleic acid molecules separated away from the nucleic acid molecules of the genomic DNA or cellular RNA of their source of origin (e.g., as it exists in cells or in a mixture of nucleic acid molecules such as a library), and may have undergone further processing. "Isolated" nucleic acid molecules include nucleic acid molecules obtained by methods described herein, similar methods or other suitable methods, including essentially pure nucleic acid molecules, nucleic acid molecules produced by chemical synthesis, by combinations of biological and chemical methods, and recombinant nucleic acid molecules which are isolated. Nucleic acid molecules referred to herein as "recombinant" are nucleic acid molecules which have been produced by recombinant DNA methodology, including those nucleic acid molecules that are generated by procedures which rely upon a method of artificial recombination, such as the polymerase chain reaction (PCR) and/or cloning into a vector using restriction enzymes. "Recombinant" nucleic acid molecules are also those that result from recombination events that occur through the natural mechanisms of cells, but are selected for after the introduction to the cells of nucleic acid molecules designed to allow and make probable a desired recombination event.

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

In certain embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

Methods by which expression vectors may be introduced into cells are known in the art. In certain embodiments of the presently disclosed subject matter, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Nicolas and Rubinstein, 1988; Baichwal and Sugden, 1986; Temin, 1986). Preferred gene therapy vectors are generally viral vectors.

II. Methods of Treatment or Prevention

In some embodiments, the presently disclosed subject matter is directed to a method of treating or preventing a Cap-Snatching virus infection, such as an influenza virus infection, in a subject in need thereof including a subject at risk of exposure to said viruses, the method comprising administering to the subject a prophylactically or therapeutically effective amount of a pharmaceutically acceptable composition comprising an expression vector comprising a polynucleotide coding sequence operably linked to a constitutive promoter, wherein the polynucleotide coding sequence encodes a precursor RNAi construct, wherein the precursor RNAi construct comprises an mRNA molecule comprising: (a) 5' methylguanosine cap leader; (b) an 8 to 12 nucleotide sequence immediately downstream from the methylguanosine cap leader; and (c) an RNAi sequence immediately downstream from the 8 to 12 nucleotide sequence; and wherein the mRNA molecule does not comprise a ribosomal binding site. In some embodiments, the 8 to 12 nucleotide sequence immediately downstream from the methylguanosine cap leader may constitute 8, 9, 10, 11, or 12 nucleotides immediately downstream from the methylguanosine cap leader. For other embodiments, cap-snatching viruses which cleave a larger leader sequence from a host mRNA would employ therapeutics matching the length of their snatched mRNA cap leader sequence.

In particular embodiments, the Cap-Snatching virus is an influenza virus, and the RNAi sequence is targeted to an influenza virus transcript, particularly wherein the RNAi sequence is an siRNA sequence selected from the group consisting of: SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40. In other embodiments, the expression vector is a lentiviral expression vector that targets host epithelial airway cells but does not integrate into host epithelial airway cell DNA, particularly wherein the host epithelial airway cell is a human epithelial airway cell. In other embodiments, the pharmaceutically acceptable composition is administered to airway epithelial cells of a subject to treat or prevent an influenza infection, particularly to nasal or intrapulmonary airway epithelial cells of the subject by direct topical application or by inhalation.

As used herein, the term "infection" refers to the invasion of a host organism's bodily tissues by disease-causing organisms, their multiplication, and the reaction of host tissues to these organisms and the toxins they produce. By "disease" is meant any condition, dysfunction or disorder that damages or interferes with the normal function of a cell, tissue, organ, or host system.

As used herein, the term "inhibit" or "inhibits" means to decrease, suppress, attenuate, diminish, arrest, or stabilize the development or progression of a disease, disorder, or condition, the activity of a biological pathway, or a biological activity, e.g., by at least 10%, 20%, 30%, 40%, 50%, 60%, 70%, 80%, 90%, 95%, 98%, 99%, or even 100% compared to an untreated control subject, cell, biological pathway, or biological activity. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

The subject treated by the presently disclosed methods in their many embodiments is desirably a human subject, although it is to be understood that the methods described herein are effective with respect to all mammalian species and avian species, which are intended to be included in the term "subject." Accordingly, a "subject" can include a human subject for medical purposes, such as for the treatment of an existing condition or disease or the prophylactic treatment for preventing the onset of a condition or disease, or an animal (particularly mammalian or avian) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Avian animal subjects include, but are not limited to chickens, turkeys, doves, ducks, pheasants, geese, quail, and any other non-domesticated birds. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The presently disclosed compositions can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

In a preferred embodiment, the presently disclosed compositions are administered to airway epithelial cells of the subject, particularly to nasal or intrapulmonary airway epithelial cells of the subject by direct topical application or by inhalation. Where the pharmaceutically acceptable composition is administered by inhalation it may be formulated as an aerosol. Aerosol usually refers to a spray that delivers a colloid of fine solid particles or liquid droplets.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin or airway epithelial cells.

Regardless of the route of administration selected, the presently disclosed compositions are formulated into pharmaceutically acceptable dosage forms such as described herein or by other conventional methods known to those of skill in the art.

The term "effective amount," as in "a therapeutically effective amount" or "a prophylactically effective amount" of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular composition employed, the route of administration, the time of administration, the rate of excretion of the particular composition being employed, the duration of the treatment, other drugs, and/or materials used in combination with the particular composition employed, the age, sex, weight, condition, general health and prior medical history of the patient being treated, and like factors well known in the medical arts.

A physician having ordinary skill in the art can readily determine and prescribe the effective amount of the composition required. Accordingly, the dosage range for administration will be adjusted by the physician as necessary.

Generally, doses of compositions will range from about 0.0001 to about 1000 mg per kilogram of body weight of the subject. In certain embodiments, the dosage is between about 1 μg/kg and about 500 mg/kg, more preferably between about 0.01 mg/kg and about 50 mg/kg. For example, in certain embodiments, a dose can be about 1, 5, 10, 15, 20, or 40 mg/kg.

By "in combination with" is meant the administration of presently disclosed compositions as described herein, with one or more therapeutic agents either simultaneously, sequentially, or a combination thereof. Therefore, a subject administered a combination of presently disclosed compositions, can receive a presently disclosed composition, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the presently disclosed compositions and one or more therapeutic agents are administered simultaneously, they can be administered to the subject as separate pharmaceutical compositions, or be administered to a subject as a single pharmaceutical composition comprising both agents.

III. Methods of Diagnosis

The presently disclosed subject matter is also directed to a method of diagnosing a Cap-Snatching virus infection in a subject. Accordingly, in some embodiments, the presently disclosed subject matter comprises a method of diagnosing a Cap-Snatching virus infection in a subject, the method comprising: (a) obtaining a biological sample from the subject, wherein the biological sample comprises cells suspected of being infected with a Cap-Snatching virus; (b) introducing a first expression vector into the cells, wherein the first expression vector comprises a first polynucleotide coding sequence operably linked to a constitutive promoter, wherein the first polynucleotide coding sequence encodes an expression product capable of producing a detectable signal, and further wherein the detectable signal is produced from the expression product in the cells; (c) obtaining a first measurement of the detectable signal produced from the expression product in the cells; (d) introducing a second expression vector into the cells, wherein the second expression vector comprises a polynucleotide coding sequence encoding a precursor RNAi construct, wherein the precursor RNAi construct comprises an mRNA molecule comprising: (i) a 5' methylguanosine cap leader; (ii) an 8 to 12 nucleotide sequence immediately downstream from the methylguanosine cap leader; and (iii) an RNAi sequence immediately downstream from the 8 to 12 nucleotide sequence, wherein the RNAi sequence is targeted to the expression product that produces a detectable label; and (e) obtaining a second measurement the detectable signal produced from the expression product in the cells; wherein a decrease in the detectable signal from the first measurement to the second measurement is indicative of a Cap-Snatching virus infection in the subject.

In other embodiments, the RNAi sequence is selected from the group consisting of an siRNA, an shRNA, a piRNA, an endo-siRNA, and an ra-siRNA. In further embodiments, the expression vector is a DNA vector or a lentiviral expression vector. In other embodiments, the Cap-Snatching virus is selected from the group consisting of an influenza virus, a hantavirus, a Rift Valley Fever virus, and a Cap-Snatching hemorrhagic virus, particularly wherein the Cap-Snatching virus is an influenza virus, and more particularly wherein the cells comprise airway epithelial cells suspected of being infected with an influenza virus.

In some embodiments, the expression product that produces a detectable label may be any peptide or polypeptide (e.g., an enzyme), that generates a detectable product (e.g., β-galactosidase, luciferase, horse radish peroxidase, alkaline phosphatase, and the like), or a protein that is itself detectable. Suitable polypeptides that generate a detectable signal include, but are not limited to, fluorescent proteins, e.g., a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or *Ptilosarcus guernyi*, as described in, e.g., WO 99/49019 and Peelle et al. (2001) *J. Protein Chem.* 20:507-519; "humanized" recombinant GFP (hrGFP) (Stratagene); a fluorescent protein as described in U.S. Pat. No. 6,969,597; any of a variety of fluorescent and colored proteins from Anthozoan species, as described in, e.g., Matz et al. (1999) *Nature Biotechnol.* 17:969-973; and the like. Suitable fluorescent proteins include, e.g., DsRed. See, e.g., Geoffrey S. Baird et al. "Biochemistry, mutagenesis, and oligomerization of DsRed, a red fluorescent protein from coral" *PNAS*, Oct. 24, 2000, vol. 97, No. 22 pp. 11984-11989. DsRed polypeptides and variants are also described in, e.g., U.S. Patent Publication No. 2005/0244921; and U.S. Pat. No. 6,969,597.

As used herein, the term a "decrease" in the detectable signal means an attenuation or diminution of the detectable signal by at least 10%, 20%, 30%, 40%, 50%, 60%, 70%, 80%, 90%, 95%, 98%, 99%, or even 100% compared to the detectable signal prior to the introduction of the second expression vector into the cells.

The term "biological sample" as used herein encompasses a variety of sample types obtained from a subject and useful in the procedure of the presently disclosed subject matter. In one embodiment of the presently disclosed subject matter, the biological sample comprises an airway epithelial cell. However, biological samples may include, but are not limited to, solid tissue samples, liquid tissue samples, biological fluids, aspirates, cells and cell fragments. Specific examples of biological samples include, but are not limited to, solid tissue samples obtained by surgical removal, pathology specimens, archived samples, or biopsy specimens, tissue cultures or cells derived therefrom and the progeny thereof, and sections or smears prepared from any of these sources. Non-limiting examples of biological samples include samples obtained from breast tissue, lymph nodes, and breast tumors. Biological samples also include any material derived from the body of a vertebrate animal, including, but not limited to, blood, cerebrospinal fluid, serum, plasma, urine, nipple aspirate, fine needle aspirate, tissue lavage such as ductal lavage, saliva, sputum, ascites fluid, liver, kidney, breast, bone, bone marrow, testes, brain, ovary, skin, lung, prostate, thyroid, pancreas, cervix, stomach, intestine, colorectal, brain, bladder, colon, nares, uterine, semen, lymph, vaginal pool, synovial fluid, spinal fluid, head and neck, nasopharynx tumors, amniotic fluid, breast milk, pulmonary sputum or surfactant, urine, fecal matter and other liquid samples of biologic origin.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

RNAi Constructs for Treating or Preventing a Cap-Snatching Virus Infection

The present experiment was designed to develop constructs that can be activated from an unactive form by the presence and replication of influenza viral RNA utilizing Cap-snatching of the host mRNA 5' Methylguanosine cap.

Cap-Snatching is a mechanism with which several classes of RNA viruses, such as influenza, prime the synthesis of their mRNA (FIG. 1). In typical Cap-Snatching, a viral RNA-dependent, RNA polymerase (RdRP) complex binds to a copy of its genomic RNA, and then subsequently binds to a host cell mRNA transcript at the 5',7-methylguanosine cap. This initiates RdRP endonuclease activity, resulting in the cleavage of approximately the first 10 nucleotides of the 5' capped host mRNA. The virus then uses this capped 10 nucleotide sequence to prime the transcription of its own RNA genome. The presently disclosed approach takes advantage of intracellular viral Cap-Snatching to activate an inactive pro-form of short RNA, and induce an anti-viral response utilizing the intracellular machinery of RNAi. Since RNAi activity is dependent on sequence-length, the cleavage of a 10 nucleotide leader sequence from a pro-(inactive) form of a short, capped RNA molecule, results in an active RNAi molecule. If Cap-Snatching activity is not present within the cell, meaning there is no replicating virus within that cell, then the proRNAi construct is degraded through normal cellular pathways, and so operates orthogonally to the cell machinery. This approach can be tailored such that any infecting virus which utilizes Cap-Snatching can activate its own therapeutic response. In addition, this strategy can be utilized for larger diagnostic and prophylactic, but nonvaccine, applications.

The presently disclosed precursor RNAi or pro-RNAi constructs are not limited to a single sequence targeting a single part of the virus. For example, constructs against both the virus and against negative regulators of host innate immunity may be used. The constructs can be used singly or in combinations.

For the anti-viral RNAi constructs, 20 siRNA sequences validated over 10 years by the greater flu community may be used (Table 1; reviewed in Barik (2010) "siRNA for Influenza Therapy," *Viruses* 2:1448-1457). These sequences target various parts of the viral machinery, with minimal off-target effects, and therefore, minimal toxicity.

TABLE 1

Validated RNAi sequences

| Target viral mRNA (nt #) | siRNA Sequence: Top Strand 5' to 3' |
|---|---|
| PB2-2210 | GGAGACGUGGUGUUGGUAAdTdT (SEQ ID NO: 1)<br>dTdTCCUCUGCACCACAACCAUU (SEQ ID NO: 2) |
| PB2-2240 | CGGGACUCUAGCAUACUUAdTdT (SEQ ID NO: 3)<br>dTdTGCCCUGAGAUCGUAUGAAU (SEQ ID NO: 4) |
| PB1-6 | GCAGGCAAACCAUUUGAAUdTdT (SEQ ID NO: 5)<br>dTdTCGUCCGUUUGGUAAACUUA (SEQ ID NO: 6) |
| PB1-129 | CAGGAUACACCAUGGAUACdTdT (SEQ ID NO: 7)<br>dTdTGUCCUAUGUGGUACCUAUG (SEQ ID NO: 8) |
| PB1-2257 | GAUCUGUUCCACCAUUGAAdTd (SEQ ID NO: 9)<br>TdTdTCUAGACAAGGUGGUAACUU (SEQ ID NO: 10) |
| PA-44 | UGCUUCAAUCCGAUGAUUGdTdT (SEQ ID NO: 11)<br>dTdTACGAAGUUAGGCUACUAAC (SEQ ID NO: 12) |
| PA-739 | CGGCUACAUUGAGGGCAAGdTdT (SEQ ID NO: 13)<br>dTdTGCCGAUGUAACUCCCGUUC (SEQ ID NO: 14) |
| PA-2087 | GCAAUUGAGGAGUGCCUGAdTdT (SEQ ID NO: 15)<br>dTdTCGUUAACUCCUCACGGACU (SEQ ID NO: 16) |
| PA-2110 | UGAUCCCUGGGUUUUGCUUdTdT (SEQ ID NO: 17)<br>dTdTACUAGGGACCCAAAACGAA (SEQ ID NO: 18) |
| PA-2131 | UGCUUCUUGGUUCAACUCCdTdT (SEQ ID NO: 19)<br>dTdTACGAAGAACCAAGUUGAGG (SEQ ID NO: 20) |
| NP-231 | UAGAGAGAAUGGUGCUCUCdTdT (SEQ ID NO: 21)<br>dTdTAUCUCUCUUACCACGAGAG (SEQ ID NO: 22) |
| NP-390 | UAAGGCGAAUCUGGCGCCAdTdT (SEQ ID NO: 23)<br>dTdTAUUCCGCUUAGACCGCGGU (SEQ ID NO: 24) |
| NP-1496 | GGAUCUUAUUUCUUCGGAGdTdT (SEQ ID NO: 25)<br>dTdTCCUAGAAUAAAGAAGCCUC (SEQ ID NO: 26) |
| M-37 | CCGAGGUCGAAACGUACGUdTdT (SEQ ID NO: 27)<br>dTdTGGCUCCAGCUUUGCAUGCA (SEQ ID NO: 28) |
| M-480 | CAGAUUGCUGACUCCCAGCdTdT (SEQ ID NO: 29)<br>dTdTGUCUAACGACUGAGGGUCG (SEQ ID NO: 30) |
| M-598 | UGGCUGGAUCGAGUGAGCAdTdT (SEQ ID NO: 31)<br>dTdTACCGACCUAGCUCACUCGU (SEQ ID NO: 32) |
| M-934 | GAAUAUCGAAAGGAACAGCdTdT (SEQ ID NO: 33)<br>dTdTCUUAUAGCUUUCCUUGUCG (SEQ ID NO: 34) |
| NS- | CGGCUUCGCCGAGAUCAGAdAdT (SEQ ID NO: 35) |

TABLE 1-continued

Validated RNAi sequences

| Target viral mRNA (nt #) | siRNA Sequence: Top Strand 5' to 3' |
|---|---|
| 128 | dTdAGCCGAAGCGGCUCUAGUCU (SEQ ID NO: 36) |
| NS-562 | GUCCUCCGAUGAGGACUCCdTdT (SEQ ID NO: 37)<br>dTdTCAGGAGGCUACUCCUGAGG (SEQ ID NO: 38) |
| NS-589 | UGAUAACACAGUUCGAGUCdTdT (SEQ ID NO: 39)<br>dTdTACUAUUGUGUCAAGCUCAG (SEQ ID NO: 40) |

For the host innate immunity constructs, there are well known host cell regulators which also have validated siRNA sequences, such as negative regulators of apoptosis, and cytokine/chemokine production. These and other host cell regulators may also be used in the presently disclosed methods.

Since influenza infections are confined to epithelial cells of the respiratory tract, the construct, such as a lentiviral vector, may be delivered through an inhaler. The construct may target epithelial-airway cells and will not integrate with host DNA, which allows the therapy to be self-limiting by dissipating with the natural turnover of airway epithelial cells, such as in about 2 weeks. Another self-limitation is the lack of stability of the transcript (precursor RNAi or pro-RNAi) itself. The transcript persists for a limited amount of time and is available for activation by Cap-Snatching, but is then degraded through normal cellular pathways like a regular transcript. In this way, it will be orthologous to normal cell operations. This approach may be modeled using influenza infection of human cells as well as primary-terminally differentiated cell culture models of the human respiratory epithelium.

The presently disclosed subject matter may also be used in broader applications, such as using an innocuous virus as genetic element "switches" to enable disease-specific treatments/diagnostics, enabled by the modularity of RNAi sequence. As another example, the presently disclosed subject matter may be modeled in mice and the mutational response of the virus may be evaluated. As still another example, the presently disclosed subject matter may be leveraged to fight other viruses that utilize Cap-Snatching activity, such as hemorrhagic fever viruses.

Exemplary RNAi constructs comprising siRNA duplexes for use in the presently disclosed methods may include the siRNA duplexes listed in Table 2 (see, e.g., Barik (2010) "siRNA for Influenza Therapy," *Viruses* 2:1448-1457; Ge et al. (2003) *Proc. Natl. Acad. Sci. U.S.A.* 100:2718-2723).

TABLE 2 siRNA duplexes*

| Construct | (+) strand length | (−) strand length | RNA Sequence (top strand is 5' to 3'; bottom strand is 3' to 5') | Target viral mRNA (nt #) | Viral protein product target |
|---|---|---|---|---|---|
| siRNA (+), NP-1496 (Life Technologies; Custom synthesized siRNA) | 23 | 23 | TOP Strand (Sequence A): GGAUCUUAUUUCUUCGGAGdTdT (SEQ ID NO: 25)<br>Bottom (Sequence B): dTdTCCUAGAAUAAAGAAGCCUC (SEQ ID NO: 26) | NP-1496 | NP (Viral Nucleocapsid Protein) |

TABLE 2-continued

| Construct | (+) strand length | (−) strand length | RNA Sequence (top strand is 5' to 3'; bottom strand is 3' to 5') | Target viral mRNA (nt #) | Viral protein product target |
|---|---|---|---|---|---|
| siRNA (+), M-37 (Life Technologies; Custom synthesized siRNA) | 23 | 23 | TOP Strand (Sequence A): CCGAGGUCGAAACGUACGUdTdT (SEQ ID NO: 27) Bottom (Sequence B): dTdTGGCUCCAGCUUUGCAUGCA (SEQ ID NO: 28) | M-37 | M (M1 or M2, viral structural protein, and lifecycle protein) |
| siRNA (+), PB-129 (Life Technologies; Custom synthesized siRNA) | 23 | 23 | TOP Strand (Sequence A): CAGGAUACACCAUGGAUACdTdT (SEQ ID NO: 7) Bottom (Sequence B): dTdTGUCCUAUGUGGUACCUAUG (SEQ ID NO: 8) | PB1-129 | PB1 (Viral RNA Transcriptase subunit) |
| siRNA (−): scramble sequence (Life Technologies; AM4611) | 23 | 23 | Silencer ® Negative Control No. 1 siRNA (Proprietary sequence of Life Technologies) | None | N/A |
| siRNA (−), scramble sequence (Life Technologies; Custom) | 33 | 23 | Add 7mGCCUAGAAUA (SEQ ID NO: 41) to the 5' end of top strand of Silencer ® Negative Control No. 1 siRNA proprietary sequence above | None; | N/A |
| NP-1496, siRNA (Life Technologies; Custom) | 33 | 23 | TOP Strand (Sequence A): 7mGCCUAGAAUAGGAUCUUAUUU CUUCGGAGdTdT (SEQ ID NO: 42) Bottom (Sequence B): dTdTCCUAGAAUAAAGAAGCCUC (SEQ ID NO: 43) | NP-1496 | NP (Viral Nucleocapsid Protein) |
| M-37, siRNA (Life Technologies; Custom) | 33 | 23 | TOP Strand (Sequence A): 7mGCCUAGAAUACCGAGGUCGAA ACGUACGUdTdT (SEQ ID NO: 44) Bottom (Sequence B): dTdTGGCUCCAGCUUUGCAUGCA (SEQ ID NO: 45) | M-37 | M (M1 or M2, viral structural protein, and lifecycle protein) |
| PB1-129, siRNA (Life Technologies; Custom) | 33 | 23 | TOP Strand (Sequence A): 7mGCCUAGAAUACAGGAUACACC AUGGAUACdTdT (SEQ ID NO: 46) Bottom (Sequence B): dTdTGUCCUAUGUGGUACCUAUG (SEQ ID NO: 47) | PB1-129 | PB1 (Viral RNA Transcriptase subunit) |

*All constructs in Table 1 were obtained from Life Technologies.

Exemplary RNAi constructs comprising shRNA for use in the presently disclosed methods may utilize the GeneClip™ U1 Hairpin Cloning System of Promega (Cat. #C8750) and DNA encoding shRNA as listed in Table 3 (see, e.g., Barik (2010) "siRNA for Influenza Therapy," Viruses 2:1448-1457; Ge et al. (2003) Proc. Natl. Acad. Sci. U.S.A. 100: 2718-2723).

TABLE 3 shRNA oligonucleotide constructs and GeneClip vector system*

| Construct | strand length | DNA Sequence (5' to 3' continuous) | Target viral mRNA (nt #) | Viral protein product target |
|---|---|---|---|---|
| (+) shRNA construct; NP-1496 sequence A, DNA oligo | 53 | TCTCGGATCTTATTTCTTCGGAGAAGTT CTCTCTCCGAAGAAATAAGATCCCT (SEQ ID NO: 48) | NP-1496, seq A | NP (Viral Nucleocapsid Protein) |
| (+) shRNA construct; NP-1496 sequence B, DNA oligo | 59 | CTGCAGCTGGATCTTATTTCTTCGGAGA GAGAACTTCTCCGAAGAAATAAGATCC GAGA (SEQ ID NO: 49) | NP-1496, seq B | NP (Viral Nucleocapsid Protein) |
| (+) shRNA construct; M-37 sequence A, DNA oligo | 53 | TCTCCCGAGGTCGAAACGTACGTAAGT TCTCTACGTACGTTTCGACCTCGGCT (SEQ ID NO: 50) | M-37, seq A | M (M1 or M2, viral structural protein, and lifecycle protein) |
| (+) shRNA construct; M-37 sequence B, DNA oligo | 59 | CTGCAGCTCCGAGGTCGAAACGTACGT AGAGAACTTACGTACGTTTCGACCTCG GGAGA (SEQ ID NO: 51) | M-37, seq B | M (M1 or M2, viral structural protein, and lifecycle protein) |
| (-) shRNA construct; Reverse sense NP-1496, sequence A DNA oligo | 53 | TCTCGAGGCTTCTTTATTCTACCAAGTT CTGGTAGAATAAAGAAGCCTCCTCT (SEQ ID NO: 52) | (-) Reverse sense NP-1496, seq A | (-) |
| (-) shRNA construct; Reverse sense NP-1496, sequence B DNA oligo | 59 | CTGCAGCTGAGGCTTCTTTATTCTACCA GAACTTGGTAGAATAAAGAAGCCTCGA GA (SEQ ID NO: 53) | (-) Reverse sense NP-1496, seq B | (-) |
| (-) length dependent shRNA construct; Reverse sense NP-1496, sequence A DNA oligo | 63 | TCTCGAGGCTTCTTGAGGCTTCTTTATT CTACCAAGTTCTGGTAGAATAAAGAAG CCTCCTCT (SEQ ID NO: 54) | (-) Reverse sense NP-1496, length dependence, seq A | (-) |
| (-) Control, length dependent shRNA construct; Reverse sense NP-1496, sequence B DNA oligo | 69 | CTGCAGAGAGGAGGCTTCTTTATTCTA CCAGAACTTGGTAGAATAAAGAAGCCT CAAGAAGCCTCGAGA (SEQ ID NO: 55) | (-) Reverse sense NP-1496, length dependence, seq B | (-) |
| NP-1496 sequence A, shRNA construct, DNA oligo | 63 | TCTCGAGGCTTCTTGGATCTTATTTCTT CGGAGAAGTTCTCTCTCCGAAGAAATA AGATCCCT (SEQ ID NO: 56) | NP-1496, seq A | NP (Viral Nucleocapsid Protein) |
| NP-1496 sequence B, shRNA construct DNA oligo | 69 | CTGCAGAGGGATCTTATTTCTTCGGAG AGAGAACTTCTCCGAAGAAATAAGATC CAAGAAGCCTCGAGA (SEQ ID NO: 57) | NP-1496, seq B | NP (Viral Nucleocapsid Protein) |
| M-37 sequence A, shRNA construct DNA oligo | 63 | TCTCGAGGCTTCTTCCGAGGTCGAAAC GTACGTAAGTTCTCTACGTACGTTTCGA CCTCGGCT (SEQ ID NO: 58) | M-37, seq A | M (M1 or M2, viral structural protein, and lifecycle protein) |
| M-37 sequence B, shRNA construct DNA oligo | 69 | CTGCAGCTCCGAGGTCGAAACGTACGT AGAGAACTTACGTACGTTTCGACCTCG GAAGAAGCCTCGAGA (SEQ ID NO: 59) | M-37, seq B | M (M1 or M2, viral structural protein, and lifecycle protein) |

TABLE 3-continued shRNA oligonucleotide constructs and GeneClip vector system*

| Construct | strand length | DNA Sequence (5' to 3' continuous) | Target viral mRNA (nt #) | Viral protein product target |
|---|---|---|---|---|
| PB-129 sequence A, shRNA construct DNA oligo | 63 | TCTCGAGGCTTCTTCAGGATACACCAT GGATACAAGTTCTCTGTATCCATGGTG TATCCTGCT (SEQ ID NO: 60) | PB-129, seq A | PB1 (Viral RNA Transcriptase subunit) |
| PB-129 sequence B, shRNA construct DNA oligo | 69 | CTGCAGCTCAGGATACACCATGGATAC AGAGAACTTGTATCCATGGTGTATCCT GAAGAAGCCTCGAGA (SEQ ID NO: 61) | PB-129, seq B | PB1 (Viral RNA Transcriptase subunit) |

*All DNA oligonucleotide sequences need a reverse compliment sequence in order to purify and clone. The Sequence A is the sense sequence and the Sequence B for each oligo is the reverse complement of Sequence A.

Exemplary RNAi constructs comprising single stranded (ss) siRNA for use in the presently disclosed methods may include ss-siRNA as listed in Table 4 (see, e.g., Barik (2010) "siRNA for Influenza Therapy," *Viruses* 2:1448-1457; Ge et al. (2003) *Proc. Natl. Acad. Sci. U.S.A.* 100:2718-2723).

TABLE 4

Construct Set #3: single-stranded siRNA

| Construct | (+) strand length | RNA Sequence (5' to 3') | Target viral mRNA (nt #) | Viral protein product target |
|---|---|---|---|---|
| (+) Control, ss-siRNA, NP-1496 | 23 | GGAUCUUAU UUCUUCGGA GdTdT (SEQ ID NO: 25) | NP-1496 | NP (Viral Nucleocapsid Protein) |
| (+) Control, ss-siRNA, M-37 | 23 | CCGAGGUCG AAACGUACG UdTdT (SEQ ID NO: 27) | M-37 | M (M1 or M2, viral structural protein, and lifecycle protein) |
| (+) Control, ss-siRNA, PB-129 | 23 | CAGGAUACA CCAUGGAUA CdTdT (SEQ ID NO: 7) | PB1-129 | PB1 (Viral RNA Transcriptase subunit) |
| (-) Control, ss-siRNA; Reverse sense of NP-1496 | 23 | CUCCGAAGA AAUAAGAUC CdTdT (SEQ ID NO: 62) | None | None |
| (-) length dependence, ss-siRNA; Reverse sense of NP-1496 | 23 | AAUAAGAUC CCUCCGAAG AAAUAAGAU CCdTdT (SEQ ID NO: 63) | None | None |
| NP-1496 ss-siRNA | 33 | 7mGCCUAGA AUAGGAUCU UAUUUCUUC GGAGdTdT (SEQ ID NO: 42) | NP-1496 | NP (Viral Nucleocapsid Protein) |
| M-37 ss-siRNA | 33 | 7mGCCUAGA AUACCGAGG UCGAAACGU ACGUdTdT (SEQ ID NO: 44) | M-37 | M (M1 or M2, viral structural protein, and lifecycle protein) |
| PB-129 ss-siRNA | 33 | 7mGCCUAGA AUACAGGAU ACACCAUGG AUACdTdT (SEQ ID NO: 46) | PB1-129 | PB1 (Viral RNA Transcriptase subunit) |

Example II

RNAi Constructs for Diagnosing a Cap-Snatching Virus Infection

For diagnostic methods, a DNA or viral construct are introduced into a cell suspected of a Cap-Snatching viral infection which contains a fluorescent indicator such as, but not limited to, Green Fluorescent Protein (GFP), which is constitutively expressed. Another DNA or viral construct is introduced into the cell with an inactivated RNAi sequence specific against the GFP sequence. These constructs are applied and internalized in vitro to suspect cells from a patient. In the presence of the Cap-Snatching viral activity on the inactive RNAi construct, the RNAi response becomes activated against the constitutively expressed GFP. This results in an RNAi response by the cell against GFP expression, and thus the loss or decrease of GFP signal which indicates the presence of Cap-Snatching viral activity.

What is claimed is:

1. A method of treating a Cap-Snatching virus infection in a subject in need thereof, the method comprising administering to the subject a therapeutically effective amount of a pharmaceutically acceptable composition comprising an expression vector comprising a polynucleotide coding sequence operably linked to a constitutive promoter, wherein the polynucleotide coding sequence encodes a precursor RNAi construct, wherein the precursor RNAi construct comprises an mRNA molecule comprising:
   (a) a 5' methylguanosine cap leader;
   (b) an 8 to 12 nucleotide sequence immediately downstream from the methylguanosine cap leader; and
   (c) an RNAi sequence immediately downstream from the 8 to 12 nucleotide sequence, the RNAi sequence comprising 20 to 25 nucleotides;
   wherein the mRNA molecule does not comprise a ribosomal binding site, and
   wherein in the presence of a Cap-Snatching virus, the 8 to 12 nucleotide sequence is removed and the RNAi sequence becomes activated.

2. The method of claim 1, wherein Cap-Snatching virus infection is an influenza infection, and wherein the RNAi sequence is targeted to an influenza virus transcript.

3. The method of claim 2, wherein the RNAi sequence is an siRNA sequence selected from the group consisting of: SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40.

4. The method of claim 2, wherein the expression vector is a lentiviral expression vector, and wherein the lentiviral expression vector targets host epithelial airway cells but does not integrate into host epithelial airway cell DNA.

5. The method of claim 4, wherein the pharmaceutically acceptable composition is administered to airway epithelial cells of the subject.

6. The method of claim 5, wherein the pharmaceutically acceptable composition is administered to nasal or intrapulmonary airway epithelial cells of the subject by direct topical application or by inhalation.

7. The method of claim 6, wherein the pharmaceutically acceptable composition is administered by inhalation and is formulated as an aerosol.

8. The method of claim 1, wherein the subject is a human subject.

9. The method of claim 1, wherein the subject is a mammalian subject.

10. The method of claim 1, wherein the subject is an avian subject.

* * * * *

SEQUENCE LISTING

<160> NUMBER OF SEQ ID NOS: 63

<210> SEQ ID NO 1
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 1
ggagacgugg uguugguaat t                                              21

<210> SEQ ID NO 2
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 2
ttccucugca ccacaaccau u                                              21

<210> SEQ ID NO 3
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 3
cgggacucua gcauacuuat t                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 4
ttgcccugag aucguaugaa u                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 5
gcaggcaaac cauuugaaut t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 6
ttcguccguu ugguaaacuu a                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 7
caggauacac cauggauact t                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 8
ttguccuaug ugguaccuau g                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 9
gaucuguucc accauugaat t                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 10
ttcuagacaa ggugguaacu u                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 11
ugcuucaauc cgaugauugt t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 12
ttacgaaguu aggcuacuaa c                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 13
cggcuacauu gagggcaagt t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 14
ttgccgaugu aacucccguu c                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

```
<400> SEQUENCE: 15
gcaauugagg agugccugat t                                              21

<210> SEQ ID NO 16
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 16
ttcguuaacu ccucacggac u                                              21

<210> SEQ ID NO 17
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 17
ugaucccugg guuuugcuut t                                              21

<210> SEQ ID NO 18
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 18
ttacuaggga cccaaaacga a                                              21

<210> SEQ ID NO 19
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 19
ugcuucuugg uucaacucct t                                              21

<210> SEQ ID NO 20
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
```

```
<223> OTHER INFORMATION: T is a thymidine nucleotide

<400> SEQUENCE: 20
ttacgaagaa ccaaguugag g                                              21

<210> SEQ ID NO 21
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 21
uagagagaau ggugcucuct t                                              21

<210> SEQ ID NO 22
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 22
ttaucucucu uaccacgaga g                                              21

<210> SEQ ID NO 23
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 23
uaaggcgaau cuggcgccat t                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 24
ttauuccgcu uagaccgcgg u                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
```

```
<222> LOCATION: (1)..(42)
<223> OTHER INFORMATION: T is a thymidine nucleotide

<400> SEQUENCE: 25
ggaucuuauu ucuucggagt t                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 26
ttccuagaau aaagaagccu c                                              21

<210> SEQ ID NO 27
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 27
ccgaggucga aacguacgut t                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 28
ttggcuccag cuuugcaugc a                                              21

<210> SEQ ID NO 29
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 29
cagauugcug acucccagct t                                              21

<210> SEQ ID NO 30
<211> LENGTH: 21
<212> TYPE: DNA
<213> ORGANISM: Artificial Sequence
<220> FEATURE:
<223> OTHER INFORMATION: siRNA
<220> FEATURE:
```

```
<221> NAME/KEY: misc_feature
<222> LOCATION: (1)..(21)
<223> OTHER INFORMATION: T is a thymidine nucleotide

<400> SEQUENCE: 30
ttgucuaacg acugaggguc g                                              21

<210> SEQ ID NO 31
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 31
uggcuggauc gagugagcat t                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 32
ttaccgaccu agcucacucg u                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 33
gaauaucgaa aggaacagct t                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 34
ttcuuauagc uuccuuguc g                                               21

<210> SEQ ID NO 35
<211> LENGTH: 21
<212> TYPE: DNA
<213> ORGANISM: Artificial Sequence
<220> FEATURE:
<223> OTHER INFORMATION: siRNA
```

<220> FEATURE:
<221> NAME/KEY: misc_feature
<222> LOCATION: (1)..(42)
<223> OTHER INFORMATION: T is a thymidine nucleotide and A at position
      20 is a deoxyadenosine nucleotide

<400> SEQUENCE: 35
cggcuucgcc gagaucagaa t                                           21

<210> SEQ ID NO 36
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide and A at position 2
      is a deoxyadenosine nucleotide

<400> SEQUENCE: 36
tagccgaagc ggcucuaguc u                                           21

<210> SEQ ID NO 37
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(42)
<223> OTHER INFORMATION: T is a thymidine nucleotide

<400> SEQUENCE: 37
guccuccgau gaggacucct t                                           21

<210> SEQ ID NO 38
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 38
ttcaggaggc uacuccugag g                                           21

<210> SEQ ID NO 39
<211> LENGTH: 21
<212> TYPE: DNA
<213> ORGANISM: Artificial Sequence
<220> FEATURE:
<223> OTHER INFORMATION: siRNA

<400> SEQUENCE: 39
ugauaacaca guucgaguct t                                           21

<210> SEQ ID NO 40
<211> LENGTH: 21
<212> TYPE: DNA
<213> ORGANISM: Artificial Sequence
<220> FEATURE:
<223> OTHER INFORMATION: siRNA
<220> FEATURE:

```
<221> NAME/KEY: misc_feature
<222> LOCATION: (1)..(21)
<223> OTHER INFORMATION: T is a thymidine nucleotide

<400> SEQUENCE: 40
ttacuauugu gucaagcuca g                                             21

<210> SEQ ID NO 41
<211> LENGTH: 10
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: (1)..(1)
<223> OTHER INFORMATION: m7g

<400> SEQUENCE: 41
gccuagaaua                                                          10

<210> SEQ ID NO 42
<211> LENGTH: 31
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(31)
<223> OTHER INFORMATION: T is a thymidine nucleotide
<220> FEATURE:
<221> NAME/KEY: modified_base
<222> LOCATION: (1)..(1)
<223> OTHER INFORMATION: m7g

<400> SEQUENCE: 42
gccuagaaua ggaucuuauu ucuucggagt t                                  31

<210> SEQ ID NO 43
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 43
ttccuagaau aaagaagccu c                                             21

<210> SEQ ID NO 44
<211> LENGTH: 31
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(31)
<223> OTHER INFORMATION: T is a thymidine nucleotide
<220> FEATURE:
<221> NAME/KEY: modified_base
<222> LOCATION: (1)..(1)
<223> OTHER INFORMATION: m7g

<400> SEQUENCE: 44
gccuagaaua ccgaggucga aacguacgut t                                  31
```

```
<210> SEQ ID NO 45
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 45
ttggcuccag cuuugcaugc a                                        21

<210> SEQ ID NO 46
<211> LENGTH: 31
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(31)
<223> OTHER INFORMATION: T is a thymidine nucleotide
<220> FEATURE:
<221> NAME/KEY: modified_base
<222> LOCATION: (1)..(1)
<223> OTHER INFORMATION: m7g

<400> SEQUENCE: 46
gccuagaaua caggauacac cauggauact t                             31

<210> SEQ ID NO 47
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(21)
<223> OTHER INFORMATION: T is a thymidine nucleotide

<400> SEQUENCE: 47
ttguccuaug ugguaccuau g                                        21

<210> SEQ ID NO 48
<211> LENGTH: 53
<212> TYPE: DNA
<213> ORGANISM: Artificial Sequence
<220> FEATURE:
<223> OTHER INFORMATION: DNA oligonucleotide

<400> SEQUENCE: 48
tctcggatct tatttcttcg gagaagttct ctctccgaag aaataagatc cct     53

<210> SEQ ID NO 49
<211> LENGTH: 59
<212> TYPE: DNA
<213> ORGANISM: Artificial Sequence
<220> FEATURE:
<223> OTHER INFORMATION: DNA oligonucleotide

<400> SEQUENCE: 49
ctgcagctgg atcttatttc ttcggagaga gaacttctcc gaagaaataa gatccgaga  59

<210> SEQ ID NO 50
```

<210> SEQ ID NO 50
<211> LENGTH: 53
<212> TYPE: DNA
<213> ORGANISM: Artificial Sequence
<220> FEATURE:
<223> OTHER INFORMATION: DNA oligonucleotide

<400> SEQUENCE: 50
tctcccgagg tcgaaacgta cgtaagttct ctacgtacgt ttcgacctcg gct    53

<210> SEQ ID NO 51
<211> LENGTH: 59
<212> TYPE: DNA
<213> ORGANISM: Artificial Sequence
<220> FEATURE:
<223> OTHER INFORMATION: DNA oligonucleotide

<400> SEQUENCE: 51
ctgcagctcc gaggtcgaaa cgtacgtaga gaacttacgt acgtttcgac ctcgggaga    59

<210> SEQ ID NO 52
<211> LENGTH: 53
<212> TYPE: DNA
<213> ORGANISM: Artificial Sequence
<220> FEATURE:
<223> OTHER INFORMATION: DNA oligonucleotide

<400> SEQUENCE: 52
tctcgaggct tctttattct accaagttct ggtagaataa agaagcctcc tct    53

<210> SEQ ID NO 53
<211> LENGTH: 57
<212> TYPE: DNA
<213> ORGANISM: Artificial Sequence
<220> FEATURE:
<223> OTHER INFORMATION: DNA oligonucleotide

<400> SEQUENCE: 53
ctgcagctga ggcttcttta ttctaccaga acttggtaga ataaagaagc ctcgaga    57

<210> SEQ ID NO 54
<211> LENGTH: 63
<212> TYPE: DNA
<213> ORGANISM: Artificial Sequence
<220> FEATURE:
<223> OTHER INFORMATION: DNA oligonucleotide

<400> SEQUENCE: 54
tctcgaggct tcttgaggct tctttattct accaagttct ggtagaataa agaagcctcc    60
tct    63

<210> SEQ ID NO 55
<211> LENGTH: 69
<212> TYPE: DNA
<213> ORGANISM: Artificial Sequence
<220> FEATURE:
<223> OTHER INFORMATION: DNA oligonucleotide

<400> SEQUENCE: 55
ctgcagagag gaggcttctt tattctacca gaacttggta gaataaagaa gcctcaagaa    60
gcctcgaga    69

<210> SEQ ID NO 56
<211> LENGTH: 63
<212> TYPE: DNA
<213> ORGANISM: Artificial Sequence

```
<220> FEATURE:
<223> OTHER INFORMATION: DNA oligonucleotide

<400> SEQUENCE: 56
tctcgaggct tcttggatct tatttcttcg gagaagttct ctctccgaag aaataagatc    60
cct                                                                  63

<210> SEQ ID NO 57
<211> LENGTH: 69
<212> TYPE: DNA
<213> ORGANISM: Artificial Sequence
<220> FEATURE:
<223> OTHER INFORMATION: DNA oligonucleotide

<400> SEQUENCE: 57
ctgcagaggg atcttatttc ttcggagaga gaacttctcc gaagaaataa gatccaagaa    60
gcctcgaga                                                            69

<210> SEQ ID NO 58
<211> LENGTH: 63
<212> TYPE: DNA
<213> ORGANISM: Artificial Sequence
<220> FEATURE:
<223> OTHER INFORMATION: DNA oligonucleotide

<400> SEQUENCE: 58
tctcgaggct tcttccgagg tcgaaacgta cgtaagttct ctacgtacgt ttcgacctcg    60
gct                                                                  63

<210> SEQ ID NO 59
<211> LENGTH: 69
<212> TYPE: DNA
<213> ORGANISM: Artificial Sequence
<220> FEATURE:
<223> OTHER INFORMATION: DNA oligonucleotide

<400> SEQUENCE: 59
ctgcagctcc gaggtcgaaa cgtacgtaga gaacttacgt acgtttcgac ctcggaagaa    60
gcctcgaga                                                            69

<210> SEQ ID NO 60
<211> LENGTH: 63
<212> TYPE: DNA
<213> ORGANISM: Artificial Sequence
<220> FEATURE:
<223> OTHER INFORMATION: DNA oligonucleotide

<400> SEQUENCE: 60
tctcgaggct tcttcaggat acaccatgga tacaagttct ctgtatccat ggtgtatcct    60
gct                                                                  63

<210> SEQ ID NO 61
<211> LENGTH: 69
<212> TYPE: DNA
<213> ORGANISM: Artificial Sequence
<220> FEATURE:
<223> OTHER INFORMATION: DNA oligonucleotide

<400> SEQUENCE: 61
ctgcagctca ggatacacca tggatacaga gaacttgtat ccatggtgta tcctgaagaa    60
gcctcgaga                                                            69
```

```
<210> SEQ ID NO 62
<211> LENGTH: 21
<212> TYPE: DNA
<213> ORGANISM: Artificial Sequence
<220> FEATURE:
<223> OTHER INFORMATION: ss-siRNA
<220> FEATURE:
<221> NAME/KEY: misc_feature
<222> LOCATION: (1)..(21)
<223> OTHER INFORMATION: T is a thymidine nucleotide

<400> SEQUENCE: 62
cuccgaagaa auaagaucct t                                               21

<210> SEQ ID NO 63
<211> LENGTH: 31
<212> TYPE: DNA
<213> ORGANISM: Artificial Sequence
<220> FEATURE:
<223> OTHER INFORMATION: ss-siRNA
<220> FEATURE:
<221> NAME/KEY: misc_feature
<222> LOCATION: (1)..(31)
<223> OTHER INFORMATION: T is a thymidine nucleotide

<400> SEQUENCE: 63
aauaagaucc cuccgaagaa auaagaucct t                                    31
```